United States Patent [19]

Ramsey, III et al.

[11] 4,253,993

[45] Mar. 3, 1981

[54] SHAMPOO IN FLAKE FORM

[75] Inventors: James C. Ramsey, III; Philip J. Schoner, both of Cincinnati, Ohio

[73] Assignee: The Procter & Gamble Company, Cincinnati, Ohio

[21] Appl. No.: 40,347

[22] Filed: May 18, 1979

[30] Foreign Application Priority Data

May 29, 1978 [PH] Philippines ............................ 21205

[51] Int. Cl.³ ..................... C11D 1/14; C11D 17/06
[52] U.S. Cl. ................................. 252/548; 252/545; 252/550; 252/DIG. 13
[58] Field of Search ........ 252/545, 548, 550, DIG. 13

[56] References Cited

U.S. PATENT DOCUMENTS

| 2,383,737 | 8/1945 | Richardson | 252/548 |
|---|---|---|---|
| 2,383,738 | 8/1945 | Richardson et al. | 252/550 X |
| 2,383,740 | 8/1945 | Tucker | 252/550 X |
| 2,619,469 | 12/1952 | Heald | 252/550 |
| 2,757,143 | 7/1956 | Katzman | 252/548 |
| 2,846,402 | 8/1958 | Lew | 252/548 |

FOREIGN PATENT DOCUMENTS

| 45-36590 | 11/1970 | Japan | 252/DIG. 13 |
|---|---|---|---|
| 448350 | 6/1936 | United Kingdom | 252/550 |
| 641455 | 8/1950 | United Kingdom | 252/550 |

*Primary Examiner*—P. E. Willis, Jr.
*Attorney, Agent, or Firm*—William H. Gould; Thomas H. O'Flaherty; Richard C. Witte

[57] ABSTRACT

A shampoo composition in the form of flakes is prepared by processing an aqueous slurry of $C_{12-14}$ alkyl sulfate, $C_{12-14}$ monoethanol amide, sodium sulfate and water. The processing step can be drum-drying, or flash-drying followed by roller-milling.

22 Claims, No Drawings

SHAMPOO IN FLAKE FORM

BACKGROUND OF THE INVENTION

Shampoo compositions of the prior art exist in a variety of physical forms, of which liquids, pastes and gels are the most common. They have sometimes taken the form of a powder comprising a mechanical mixture of dry ingredients, some of which may have been spray dried to form relatively homogeneous particles.

A new physical form for shampoo compositions has now been developed: dry flakes. This is an old physical form which has been used for many materials in dry form, including surfactants. So far as is known, this form has not been used heretofore for shampoo compositions, and particularly for the specific shampoo compositions of this invention.

As compared with conventional dry shampoo compositions, the flaked shampoo of this invention is not only distinctive in appearance but also cakes less, is less dusty, has a more uniform color, and creates a better size impression. Performance of the flaked shampoo is good as to cleaning of the hair, speed of lathering, and stability of lather.

SUMMARY OF THE INVENTION

In its compositional embodiment, this invention is a shampoo composition comprising, in percentages by weight based on the total composition, from 40% to 60% sodium alkyl sulfate wherein the alkyl moiety has 12 or 14 carbon atoms; from 2% to 5% alkyl monoethanol amide wherein the alkyl moiety has 12 or 14 carbon atoms; from 20% to 50% sodium sulfate; and from 1% to 7% water; wherein said composition is in the form of flakes having a thickness of from 0.070 mm. to 0.340 mm. and a bulk density from 0.28 gm./cc. to 0.44 gm./cc.; and wherein said flakes are prepared by processing a slurry containing the aforesaid components and having a moisture content of from 45% to 75% by weight of the slurry.

In its procedural embodiment, this invention is a method for preparing a shampoo is in the form of flakes which comprises (a) preparing a detergent slurry having a moisture content of from 45% to 75% by weight of the slurry by mixing sodium alkyl sulfate, alkyl monoethanol amide, sodium sulfate and water; and (b) processing said slurry to form detergent flakes having a thickness of from 0.070 mm. 0.340 mm. and a bulk density of from 0.28 to 0.44 gm./cm.; wherein said flakes comprise, in percentages by weight based on the detergent composition, from 40% to 60% sodium alkyl sulfate wherein the alkyl moiety has 12 or 14 carbon atoms; from 2% to 5% alkyl monoethanol amide wherein the alkyl moiety has 12 or 14 carbon atoms; from 20% to 50% sodium sulfate; and from 1% to 7% water. The processing step can be drum-drying, or flash-drying followed by roller-milling.

DETAILS OF THE INVENTION

Composition

One essential element of this invention is sodium $C_{12-14}$ and alkyl sulfate surfactant which is the primary cleaning and lathering agent. A common source of the alkyl moiety of this surfactant, which is sometimes called lauryl sulfate, is coconut oil. It may also be derived synthetically, as for example by the Ziegler process. The distribution of alkyl groups can vary, depending on their source and whether fractionation is employed. Frequently substantial amounts of $C_{16}$ alkyl sulfate will also be present, together with lesser amounts of $C_{10}$ and $C_{18}$. However the sudsing characteristics required for a shampoo require that the sum of the $C_{12}$ and $C_{14}$ fractions are between 40% and 60% of the shampoo composition by weight, preferably between 52% and 56%.

A second essential element is $C_{12-14}$ monoethanol amide which is used as lather stabilizer. The specification of alkyl moiety is governed by the same considerations as those described above for the surfactant. The sum of the $C_{12}$ and $C_{14}$ fractions are between 2% and 5% of the shampoo composition by weight, preferably between 3% and 4%.

A third essential element is sodium sulfate in an amount from 20% to 50% by weight of the shampoo composition preferably from 30% to 40%. A fourth essential element is water in an amount from 1% to 7% by weight of the shampoo composition, preferably from 1% to 4%.

Optional elements of the invention are colorants, especially at levels from 0.01% to 0.1% by weight of the composition; perfume, especially at levels from 0.1% to 4% by weight of the composition, and numerous minor ingredients well known to the shampoo arts. Two optional elements may be mentioned specifically: up to 3% sodium chloride by weight of the composition, preferably from 1% to 3%, and from 0.1% to 1.0% by weight of the composition, preferably from 0.3% to 0.7%, of a pH buffer. A preferred buffer for a pH of about 7 is citric acid. A number of other pH buffers are well-known in the chemical and detergent arts; among them may be mentioned organic acids and salts thereof such as maleic, oxalic, malonic, succinic, glutaric, adipic, pimelic, phthalic, tartaric, lactic and benzoic; and inorganic acids and salts thereof such as ortho-, pyro-, and triphosphonates, ortho- and meta-borates, carbonates, and silicates.

Process

A slurry is prepared by mixing the essential elements of the invention, sodium $C_{12-14}$ alkyl sulfate, $C_{12-14}$ monoethanol amide, sodium sulfate, and water, with enough additional water to bring the total moisture content of the slurry to from 45% to 75% by weight of the slurry, preferably from 55% to 65%. Sodium chloride, pH buffer and colorant may optionally be present in the slurry.

Temperature of the slurry is preferably from 80° to 200° F., more preferably from 100° to 140° F. Viscosity of the slurry is preferably from 100 to 10,000 centipoises, more preferably from 1,000 to 5,000 centipoises, when measured by a Brookfield rotating viscometer using a no. 6 spindle at a speed of 100 rpm.

Flakes are formed by one of two methods. One method is drum-drying: the slurry is pumped into the trough between two heated rolls, water is removed, and the sheet of hot, dried material which forms on the drum is removed by a doctor blade. Upon cooling, this sheet breaks up into the form of flakes. A single roll drum-dryer can be used if desired.

An alternative method is flash-drying followed by roller-milling. Hot slurry is flashed into a chamber having a relatively lower pressure; water flashes off; and the resultant dried material, while still plastic, is passes through a roller mill. One or more rolls can be chilled if desired. Slurry can be heated to above its atmospheric boiling point and then flashed into an open receiver; or alternatively slurry can be flashed into a vacuum receiver; or alternatively a combination of those techniques can be employed, as is well known in the detergent art.

Roller-milling can be accomplished on a mill having one or more, usually 2, 3, 4 or more rolls, as is also well known in the art. The sheet coming off the roller mill is removed by a doctor blade and broken up into flakes in a manner comparable to that from a drum dryer.

Flake thickness is from 0.070 mm. to 0.340 mm., preferably from 0.140 mm. to 0.270 mm. Measurement can be made by any convenient device that does not shatter the flakes, for example a micrometer or a film thickness gauge.

Bulk density of the flakes is from 0.28 to 0.44 gm./cc., preferably from 0.34 to 0.40 gm./cc. The term bulk density as used herein is not the density of individual flakes, but that of a mass of flakes when they are poured gently into a volumetric measure.

Conventional techniques of sieving, grinding and recycling can be used to control particle size. It will be appreciated that the flakes are in the form of irregularly shaped two-dimensional sheets having a relatively constant thickness as determined by the distance between the rolls of the drum dryer or the roller mill. The term particle size as used herein refers to apparent size resulting from the fractionation that occurs when flakes are subjected to screening using a standard set of U.S. sieves, and is a size intermediate between the major and minor dimensions of the particle. Opening sizes for certain U.S. standard sieves are: 70 mesh—0.208 mm.; 60 mesh—0.246 mm.; 50 mesh—0.295 mm.; 40 mesh—0.417 mm.; 30 mesh—0.589 mm.; 20 mesh—0.833 mm. While the flake particle size is not critical to this invention, the size as defined hereinbefore that is preferred is from 0.208 mm. to 0.833 mm., preferably from 0.246 mm. to 0.589 mm.

Perfume, when used, is preferably added to the flakes after drying to avoid volatilization and consequent loss during the drying process. Other optional ingredients may if desired be mechanically mixed with the flakes.

The sodium sulfate is useful in the composition as a free-flowing crystalline component which contributes toward free-flowing, non-caking properties of the flakes. Sodium chloride affects the phases of the slurry, the mechanism and process of drying, and the bulk density and degree of flexibility/brittleness of the flakes; hence sodium chloride can be used as a means for controlling the physical properties of the flakes as may be desired.

Utility

The flakes of this invention are used by putting a small quantity onto the palm of one's (usually, wet) hand, applying it to wet hair, and rubbing. This is the same method used for conventional dry shampoos, and substantially the same as for shampoos in liquid or gel form.

EXAMPLE I

A 40% solids slurry was prepared having the following composition:

| | |
|---|---|
| Na lauryl sulfate (69% $C_{12}$, 29% $C_{14}$, 2% $C_{16}$) | 50.2 parts by weight |
| coconut monoethanol amide | 3.5 |
| sodium sulfate | 36.7 |
| sodium chloride | 2.0 |
| citric acid | 0.15 |
| colorant | 0.045 |
| miscellaneous | 4.605 |
| water | 145.8 |
| total parts | 243.0 |

The 0.15 parts of citric acid adjusted the slurry pH to 6.6. Slurry temperature was 120° F. and slurry viscosity (Brookfield no. 6 spindle, 100 rpm.) was about 2500 centipoises.

The slurry was drum-dried to a moisture level of 2.0%, and 0.8% perfume was sprayed on to an agitating bed of flakes. At this point the numerical figures for "parts by weight" of solids in the slurry in the table hereinabove can be read as "percent by weight" of solids in the drum-dried shampoo composition. The pH of the finished flakes, measured as a 2% concentration in water, was 7.0.

Flake thicknesses were from 0.133 mm. to 0.274 mm. After removal of coarse (ON 20 mesh) and fine (THRU 70 mesh) fractions, the particle sizes as defined hereinabove were between 0.208 mm. and 0.833 mm. Bulk density was 0.38 gm./cc.

The drum-dried flakes were visually attractive, of relatively uniform color and particle size, free-flowing, and substantially dust-free. The flakes cleaned the hair well, lathered quickly, and maintained lather well. As compared with a conventional dry powder shampoo, the flakes had better and more uniform color, were more free-flowing, had less dust, and were lighter in bulk density (the dry shampoo had a bulk density of 0.53).

EXAMPLES II-V

Slurries are prepared and dried as described in the following table, Examples II, III, IV and V. Dried flakes resulting therefrom are satisfactory shampoo compositions in both performance and physical properties.

| | II | III | IV | V |
|---|---|---|---|---|
| Flake Composition (wt. %) | | | | |
| Na—$C_{12}$ alkyl sulfate | 40 | 0 | 30 | 16 |
| Na—$C_{14}$ alkyl sulfate | 0 | 60 | 22 | 40 |
| $C_{12}$ monoethanol amide | 2 | 3 | 2 | 0 |
| $C_{14}$ monoethanol amide | 2 | 2 | 0 | 3 |
| sodium sulfate | 50 | 20 | 40 | 30 |
| sodium chloride | 0 | 3 | 1 | 2 |
| citric acid | 0.7 | 0.1 | 0.3 | 1.0 |
| miscellaneous | 2.3 | 4.9 | 3.7 | 3.0 |
| water | 3 | 7 | 1 | 5 |
| | 100.0 | 100.0 | 100.0 | 100.0 |
| Slurry Properties | | | | |
| moisture (wt. %) | 45 | 55 | 75 | 65 |
| temperature (°F.) | 200 | 140 | 80 | 100 |
| Method of Processing | | | | |
| Drum-drying | x | | | x |
| Flash-drying/roller-milling | | x | x | |

Example II is varied by preparing slurries having higher moisture levels and lower temperatures, producing thereby slurry viscosities of 100, 1000, 5000 and 10000 centipoises, respectively. Example III is similarly varied to produce bulk densities of 0.32, 0.34, 0.40, and 0.44 gm./cc.

The flash-dried slurry of Example IV is roller-milled with clearances between the rolls varied so as to yield flakes having thicknesses of 0.070, 0.140, 0.270 and 0.340 mm., respectively. The flakes of Example V are screened in such a manner to yield the following particle size distribution (wt.%) for samples a/b/c/d (U.S. standard sieves):

|  | a | b | c | d |
|---|---|---|---|---|
| through 20 on 30 mesh | 60% | — | — | 30% |
| through 30 on 60 mesh | 40% | 30% | 100% | 40% |
| through 60 on 70 mesh | — | 70% | — | 30% |

What is claimed:

1. A shampoo composition comprising, in percentages by weight based on the total composition, from 40% to 60% sodium alkyl sulfate wherein the alkyl moiety has 12 or 14 carbon atoms; from 2% to 5% alkyl monoethanol amide wherein the alkyl moiety has 12 or 14 carbon atoms; from 20% to 50% sodium sulfate; and from 1% to 7% water;

wherein said composition is in the form of flakes having a thickness of from 0.070 mm. to 0.340 mm. and a bulk density from 0.28 gm./cc. to 0.44 gm./cc.; and wherein said flakes are prepared by processing a slurry containing the aforesaid components and having a moisture content of from 45% to 75% by weight of the slurry.

2. The composition of claim 1 wherein the slurry is processed by drum-drying.

3. The composition of claim 1 wherein the slurry is processed by flash-drying followed by roller-milling.

4. The composition of claim 1 which also contains from 0.1 to 1.0% by weight of the composition of a pH buffer.

5. The composition of claim 4 wherein the buffer is citric acid.

6. The composition of claim 1 which also contains from 1% to 3% sodium chloride.

7. The composition of claim 4 which also contains from 1% to 3% sodium chloride, from 0.01% to 0.10% colorant, and from 0.10% to 2.0% perfume.

8. The composition of claim 1 wherein the sodium alkyl sulfate is from 52% to 56%; the alkyl monoethanol amide is from 3% to 4%; the sodium sulfate is from 30% to 40%, and the water is from 1% to 4%; and which also contains from 0.3% to 0.7% citric acid; from 1% to 3% sodium chloride; from 0.01% to 0.10% colorant; and from 0.10% to 4.0% perfume.

9. The composition of claim 1 wherein the flake thickness is from 0.140 mm. to 0.270 mm. and the bulk density is from 0.34 to 0.40 gm./cc.

10. The composition of claim 8 wherein the flake thickness is from 0.140 mm. to 0.270 mm.; and bulk density is from 0.34 to 0.40 gm./cc., and the moisture content of the slurry is from 55% to 65% by weight of the slurry.

11. The composition of claim 10 wherein the flakes have a particle size from 0.208 mm. to 0.833 mm. and wherein the slurry has a temperature from 100° F. to 140° F. and a Brookfield viscosity of from 1000 cp. to 5000 cp. when measured at 100 rpm using a no. 6 spindle.

12. The composition of claim 10 wherein the slurry is processed by drum-drying.

13. The composition of claim 10 wherein the slurry is processed by flash-drying followed by roller-milling.

14. A method for preparing a shampoo in the form of flakes which comprises (a) preparing a detergent slurry having a moisture content of from 45% to 75% by weight of the slurry by mixing sodium alkyl sulfate, alkyl monoethanol amide, sodium sulfate and water and (b) processing said slurry to form detergent flakes having a thickness of from 0.070 mm. to 0.340 mm. and a bulk density of from 0.28 to 0.44 gm./cc.; wherein said flaskes comprise, in percentages by weight based on the detergent composition, from 40% to 60% sodium alkyl sulfate wherein the alkyl moiety has 12 or 14 carbon atoms; from 2% to 5% alkyl monoethanol amide wherein the alkyl moiety has 12 or 14 carbon atoms; from 20% to 50% sodium sulfate; and from 1% to 7% water.

15. The method of claim 14 where said processing step is drum-drying.

16. The method of claim 14 where said processing step comprises flash-drying followed by roller-milling.

17. The method of claim 14 wherein said slurry has a temperature of from 80° F. to 200° F. and a Brookfield viscosity of from 100 cp. to 10,000 cp. when measured at 100 rpm using a no. 6 spindle.

18. The method of claim 17 wherein the flake thickness is from 0.140 mm. to 0.270 mm.; the bulk density is from 0.34 to 0.40 gm./cc.; the particle size is from 0.28 mm. to 0.833 mm.; the moisture content of the slurry is from 55% to 65% by weight of the slurry; the slurry temperature is from 100° F. to 140° F.; and the Brookfield viscosity is from 1000 cp. to 5000 cp. when measured at 100 rpm using a no. 6 spindle.

19. The method of claim 18 wherein the weight of the composition the sodium sulfate is from 52% to 56%; the alkyl monoethanol amide is from 3% to 4% the sodium sulfate is from 30% to 40% and the water is from 1% to 4%.

20. The method of claim 19 wherein the composition also contains, by weight of the composition, from 0.3% to 0.7% citric acid; from 1% to 3% sodium chloride; from 0.01% to 0.10% colorant; and from 0.10% to 4.0% perfume.

21. The method of claim 20 where said processing step is drum-drying.

22. The method of claim 20 where said processing step comprises flash-drying followed by roller-milling.

* * * * *